United States Patent
Fujisaki

(10) Patent No.: US 11,806,469 B2
(45) Date of Patent: *Nov. 7, 2023

(54) NEGATIVE PRESSURE WOUND THERAPY DEVICE

(71) Applicant: Murata Manufacturing Co., Ltd., Kyoto (JP)

(72) Inventor: Masaaki Fujisaki, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 716 days.

This patent is subject to a terminal disclaimer.

(21) Appl. No.: 16/919,172

(22) Filed: Jul. 2, 2020

(65) Prior Publication Data

US 2020/0330658 A1 Oct. 22, 2020

Related U.S. Application Data

(63) Continuation of application No. 15/397,815, filed on Jan. 4, 2017, now Pat. No. 10,737,003, which is a (Continued)

(30) Foreign Application Priority Data

Jul. 7, 2014 (JP) .................................. 2014-139719

(51) Int. Cl.
*A61M 1/00* (2006.01)
*A61F 13/00* (2006.01)

(52) U.S. Cl.
CPC ....... *A61M 1/962* (2021.05); *A61F 13/00008* (2013.01); *A61F 13/00068* (2013.01); (Continued)

(58) Field of Classification Search
CPC ........ A61M 1/009; A61M 1/962; A61M 1/73; A61M 1/74; A61M 1/80; A61M 1/78; (Continued)

(56) References Cited

U.S. PATENT DOCUMENTS 8,764,732 B2* 7/2014 Hartwell ........... A61F 13/00063
604/319
9,295,586 B2* 3/2016 Locke ................. A61F 13/0216
(Continued)

FOREIGN PATENT DOCUMENTS

JP 2009-536851 A 10/2009
JP 2012-525202 A 10/2012
(Continued)

OTHER PUBLICATIONS

International Search Report for PCT/JP2015/068283 dated Sep. 15, 2015.
(Continued)

*Primary Examiner* — Andrew J Mensh
(74) *Attorney, Agent, or Firm* — Pearne & Gordon LLP

(57) ABSTRACT

A housing of a pump unit is fixed to a drape of a wound dressing by a joint portion. A suction chamber that is brought into a negative pressure by driving of a piezoelectric pump directly communicates with a closed space through an opening and an inlet. Hence, a therapy device does not need to include a pipe that allows the closed space and the pump unit to communicate with each other. Therefore, since the therapy device does not need to include the pipe that allows the pump unit to communicate with the closed space, detachment of the pump unit from the wound dressing owing to coming-off of the pipe is avoided. Since the housing is fixed to the drape by the joint portion, the pump unit can be prevented from detaching from the wound dressing.

17 Claims, 9 Drawing Sheets

Related U.S. Application Data continuation of application No. PCT/JP2015/068283, filed on Jun. 25, 2015.

(52) U.S. Cl.
CPC ................ *A61M 1/73* (2021.05); *A61M 1/74* (2021.05); *A61M 1/78* (2021.05); *A61M 1/80* (2021.05); *A61M 1/784* (2021.05); *A61M 2205/42* (2013.01); *A61M 2205/8206* (2013.01)

(58) Field of Classification Search
CPC .. A61M 1/784; A61M 1/0025; A61M 1/0031; A61M 1/0049; A61M 1/0066; A61M 1/0052; A61M 2205/42; A61M 2205/8206; A61F 13/00008; A61F 13/00068

USPC ........................................................ 604/320
See application file for complete search history.

(56) References Cited

U.S. PATENT DOCUMENTS

| | | | |
|---|---|---|---|
| 10,737,003 B2* | 8/2020 | Fujisaki | A61F 13/00068 |
| 2007/0265586 A1* | 11/2007 | Joshi | A61F 13/0213 |
| | | | 604/313 |
| 2008/0082059 A1 | 4/2008 | Fink et al. | |
| 2011/0112492 A1* | 5/2011 | Bharti | A61M 1/78 |
| | | | 604/319 |
| 2011/0264062 A1* | 10/2011 | Locke | H01M 8/16 |
| | | | 604/319 |
| 2012/0016322 A1 | 1/2012 | Coulthard | |
| 2012/0046625 A1 | 2/2012 | Johannison | |

FOREIGN PATENT DOCUMENTS

| | | |
|---|---|---|
| JP | 2013-529357 A | 7/2013 |
| JP | 2013-538071 A | 10/2013 |
| JP | 2013-255824 A | 12/2013 |

OTHER PUBLICATIONS

Written Opinion for PCT/JP2015/068283 dated Sep. 15, 2015.
Single Use Negative Pressure Wound Therapy NPWT | Smith & Nephew-Corporate, [online], [searched on Jun. 27, 2014], the Internet (URL:http://www.smithnephew.com/key-products/advanced-wound-management/pico/).

\* cited by examiner

FIG. 4
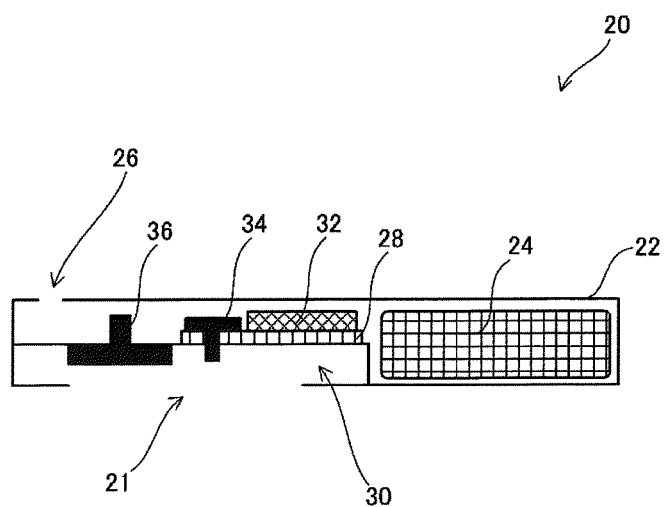
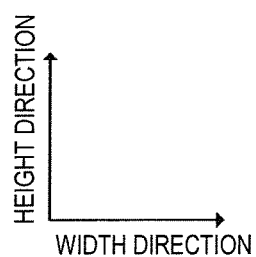

FIG. 6
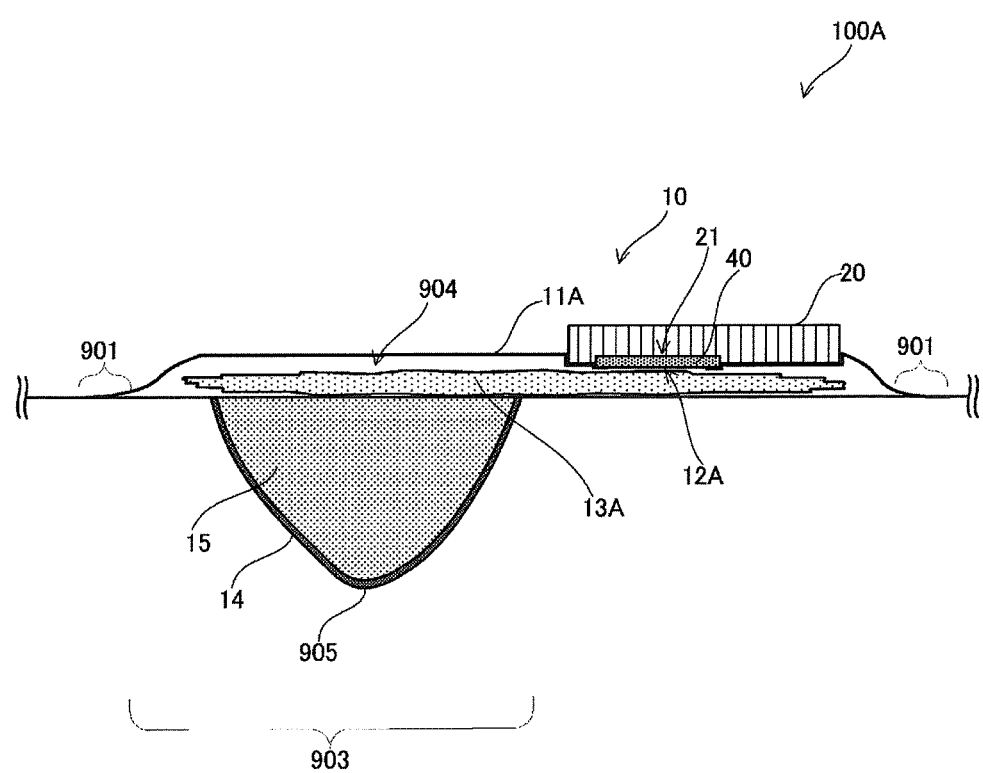
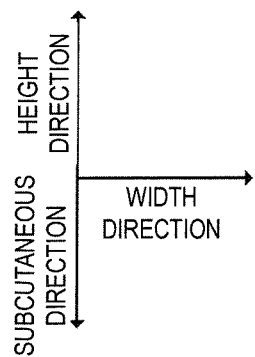

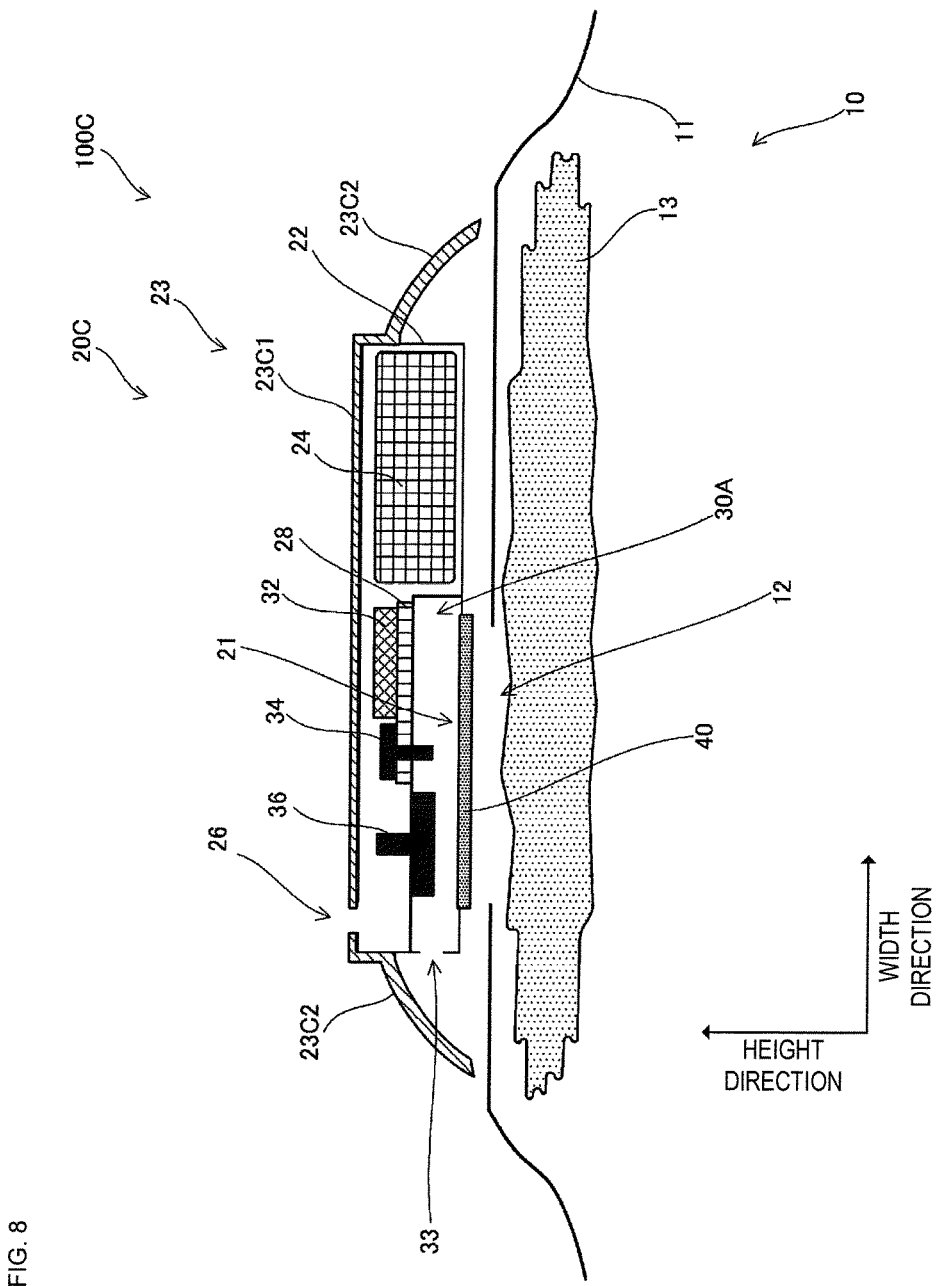

NEGATIVE PRESSURE WOUND THERAPY DEVICE

This is a continuation of U.S. patent application Ser. No. 15/397,815 filed on Jan. 4, 2017, which is a continuation of International Application No. PCT/JP2015/068283 filed on Jun. 25, 2015 which claims priority from Japanese Patent Application No. 2014-139719 filed on Jul. 7, 2014. The contents of these applications are incorporated herein by reference in their entireties.

BACKGROUND OF THE DISCLOSURE

Field of the Disclosure

The present disclosure relates to a negative pressure wound therapy device that accelerates recovery of a wound site by applying a negative pressure to a surface of the wound site.

Description of the Related Art

There has recently been known a negative pressure wound therapy that accelerates recovery of a wound site by applying a negative pressure to a surface of the wound site. For example, Patent Document 1 discloses a negative pressure wound therapy device including a wound dressing to be in close contact with an outer periphery of a wound site and a pump unit that sucks fluid from a closed space formed by the wound dressing and the wound site.

Specifically, the negative pressure wound therapy device described in Patent Document 1 includes a pipe that allows the pump unit and the closed space to communicate with each other. In the negative pressure wound therapy device described in Patent Document 1, the pump unit generates a negative pressure in the closed space by sucking gas from the closed space through the pipe. Further, in the negative pressure wound therapy device of Patent Document 1, the pump unit also sucks an exudate exuding from the surface of the wound site through the pipe.

While the pipe transports liquid and gas in the negative pressure wound therapy device of Patent Document 1, a pipe transports only gas from a closed space in a negative pressure wound therapy device described in Non-Patent Document 1.

Patent Document 1: Japanese Unexamined Patent Application Publication No. 2013-255824

Non-Patent Document 1: Single Use Negative Pressure Wound Therapy NPWT 1 Smith & Nephew-Corporate, [online], [searched on Jun. 27, 2014], the Internet (URL: http://www.smith-nephew.com/key-products/advanced-wound-management/pico/)

BRIEF SUMMARY OF THE DISCLOSURE

Since the negative pressure wound therapy device described in Patent Document 1 includes the pipe, the pipe may come off by being caught on an object present around the user. Similarly, in the negative pressure wound therapy device described in Non-Patent Document 1, the pipe may come off by being caught on an object present around the user. Therefore, in the negative pressure wound therapy devices described in Patent Document 1 and Non-Patent Document 1, the pump unit may be detached from the wound dressing by coming-off of the pipe.

Accordingly, an object of the present disclosure is to provide a negative pressure wound therapy device that prevents a pump unit from detaching from a wound dressing.

The present disclosure provides a negative pressure wound therapy device including a wound dressing including a drape having an opening and provided to be in close contact with an outer periphery of a wound site on an outer periphery of the opening, and a pump unit including a housing and a pump. In the negative pressure wound therapy device of the present disclosure, the housing includes a suction chamber communicating with a suction port of the pump, a joint portion joined to the drape, and an inlet communicating with the suction chamber in an inner side portion of the joint portion. The suction chamber directly communicates with a closed space formed by the drape and the wound site through the opening and the inlet.

In the present disclosure, the pump unit is fixed to the wound dressing because the joint portion of the housing is joined to the drape. The pressure in the suction chamber of the housing becomes a negative pressure when the pump is driven. Since the closed space directly communicates with the suction chamber through the opening and the inlet, the pressure in the closed space becomes a negative pressure when the pump is driven. Since the suction chamber directly communicates with the closed space through the opening and the inlet, the negative pressure wound therapy device does not need to include a pipe that allows the pump unit to communicate with the closed space.

As described above, since the negative pressure wound therapy device of the present disclosure does not need to include the pipe that allows the pump unit to communicate with the closed space, the pump unit is not detached from the wound dressing owing to coming-off of the pipe. Moreover, since the pump unit is fixed to the wound dressing by the joint portion of the housing, it can be prevented from detaching from the wound dressing.

As for storage of an exudate from the wound site, the negative pressure wound therapy device may further include an absorbing member disposed in the closed space to absorb liquid and a filter that allows passage of only gas and covers the inlet.

The exudate is absorbed by the absorbing member. Since the exudate does not pass through the filter, it does not flow into the suction chamber and the pump through the inlet. Therefore, the pump unit does not need to include a structure for separating an electric structure, such as a battery, from the exudate. Hence, the pump unit is smaller than when it includes the structure.

The pump unit may further include a suction pad that fixes the housing to the drape by suction.

Thus, since the housing is not easily detached from the drape of the wound dressing in the negative pressure wound therapy device, the pump unit can be further prevented from detaching from the wound dressing.

Further, the housing may include a pressure sensor that detects a pressure value in the suction chamber, and the pump unit may include a battery that supplies power to the pump and the pressure sensor, a controller that controls driving of the pump according to the pressure value detected by the pressure sensor, and a second housing that stores the battery and the controller and is electrically connected to the housing through a wire.

In this aspect, the battery and the controller are stored in the second housing. Even in this aspect, the negative pressure wound therapy device also does not need to include a pipe that allows the pump unit to communicate with the closed space. Since the housing does not need to include the battery and so on in this aspect, it is reduced in size and is less likely to detaching from the wound dressing.

The pump preferably includes a check valve that prevents backflow of fluid.

According to this structure, in the negative pressure wound therapy device, the check valve can prevent the fluid from flowing back to the closed space, for example, even when the battery is consumed and the pump cannot be driven.

The pump is preferably driven by a piezoelectric element.

That is, the pump unit preferably includes a piezoelectric pump. For example, the piezoelectric pump includes a piezoelectric element and a vibration plate joined to the piezoelectric element. The piezoelectric element expands and contracts in the surface direction of the principal surface when an alternative voltage is applied thereto. The piezoelectric pump converts this expansion and contraction into bending vibration of the vibration plate to transport the fluid from the suction port to a discharge port. The piezoelectric pump is more easily reduced in size than an electromagnetic pump or the like. Also, the piezoelectric pump is excellent in that vibrations are smaller than in the electromagnetic pump or the like. Further, when the frequency of the alternating voltage is set to be 20 kHz or more, vibration noise of the vibration plate is not easily heard by the user because the frequency becomes 20 kHz or more out of the audible frequency band.

Since the negative pressure wound therapy device of the present disclosure does not need the pipe that allows the pump unit to communicate with the closed space formed by the wound site and the drape, detachment of the pump unit from the wound dressing due to coming-off of the pipe is prevented. Moreover, since the pump unit is fixed to the wound dressing by the joint portion of the housing, it can be prevented from detaching from the wound dressing.

BRIEF DESCRIPTION OF THE SEVERAL VIEWS OF THE DRAWINGS

FIG. 4 is an enlarged sectional side view of a pump unit in the therapy device of the first embodiment.

FIG. 6 is a sectional side view of a therapy device according to a modification of the therapy device of the first embodiment.

FIG. 8 is an enlarged sectional side view of a therapy device according to a third embodiment.

DETAILED DESCRIPTION OF THE DISCLOSURE

Figure 1A:
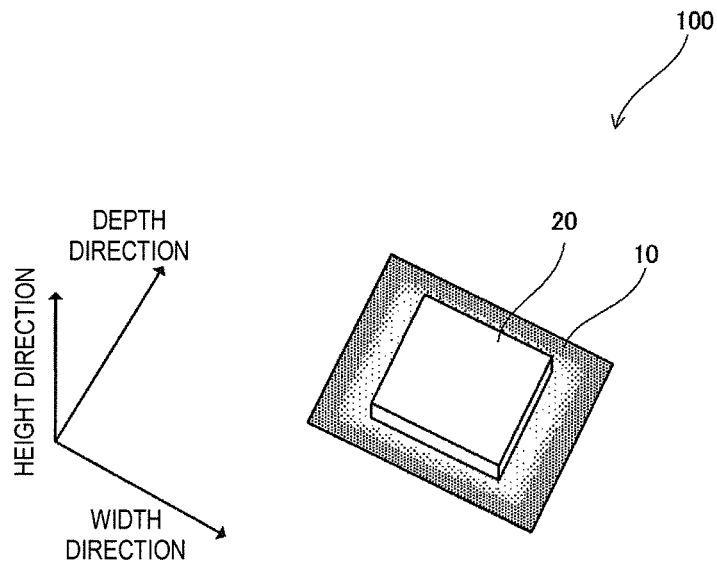
FIG. 1A is a perspective view of a therapy device according to a first embodiment, as viewed from the upper side.
Figure 1B:
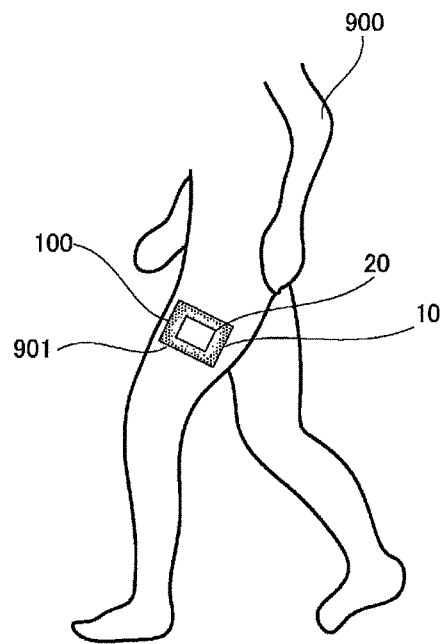
FIG. 1B illustrates an exemplary wearing manner of the therapy device of the first embodiment.
Figure 2:
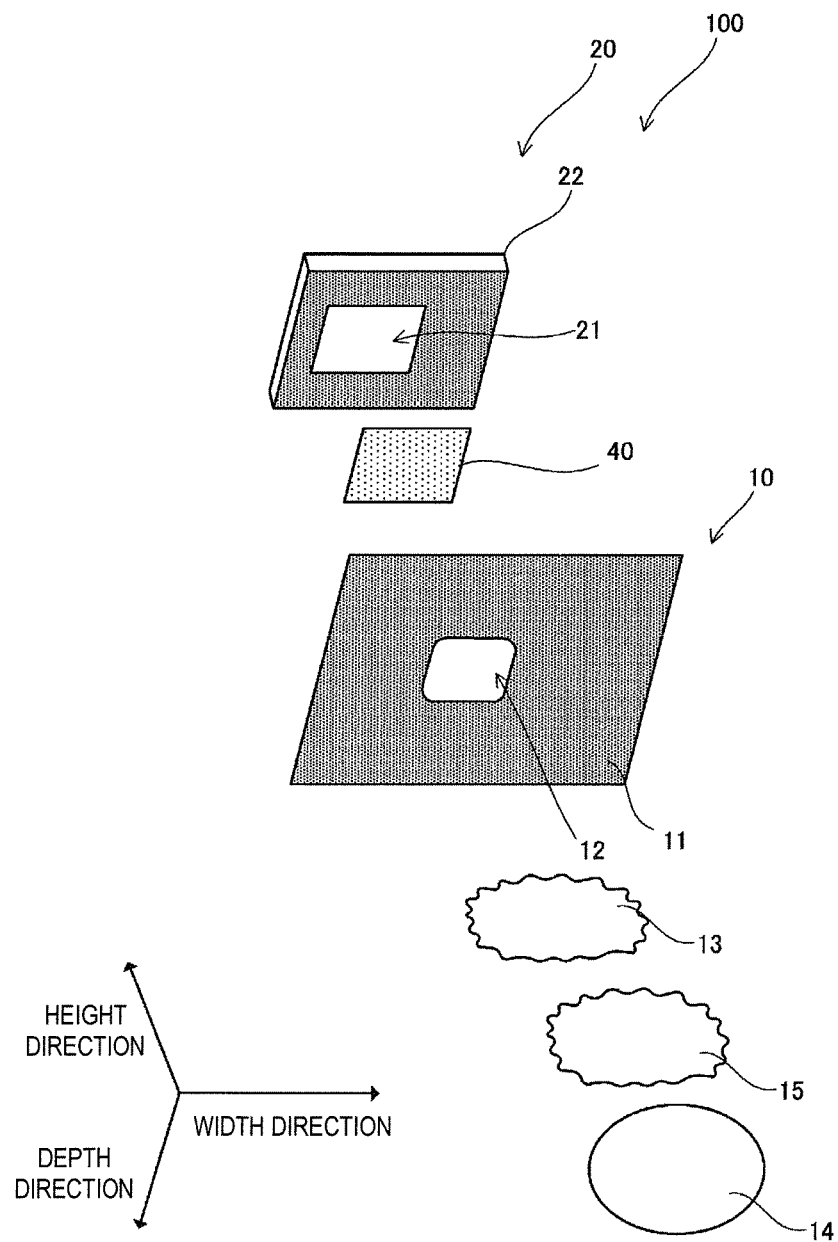
FIG. 2 is a perspective view illustrating a state in which structures of the therapy device of the first embodiment are exploded in the height direction.
Figure 3:
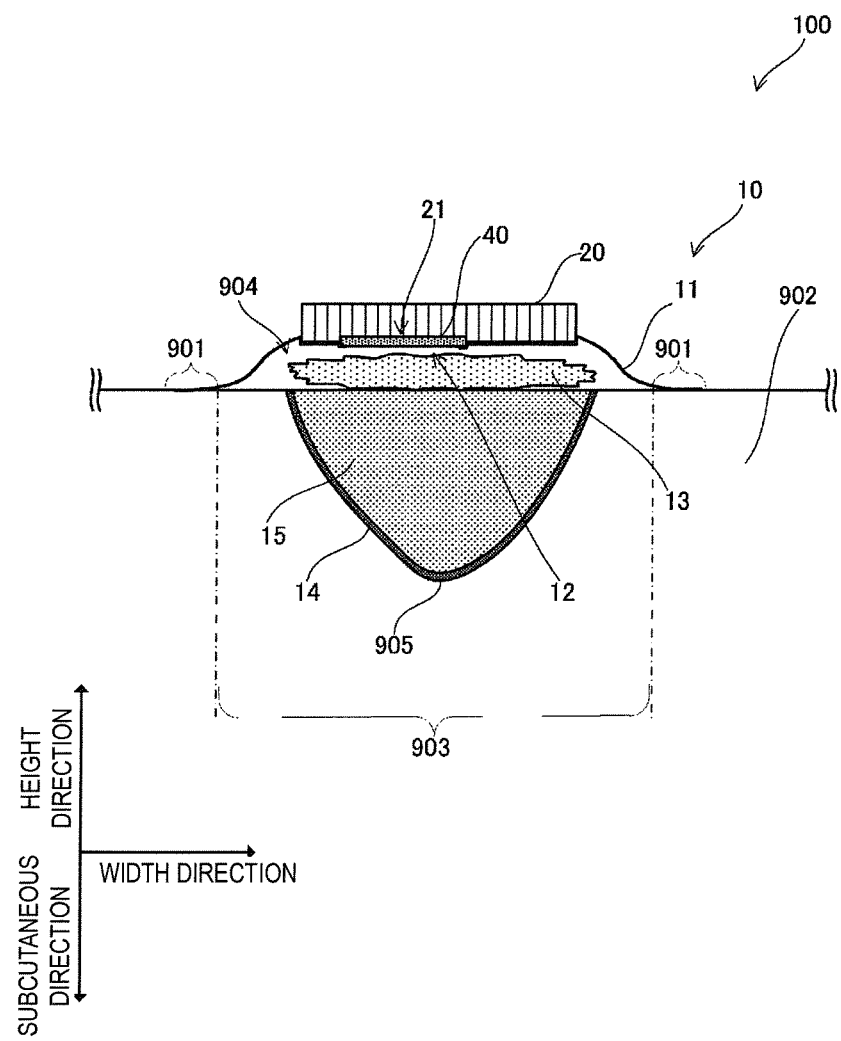
FIG. 3 is a sectional side view of the therapy device of the first embodiment in a worn state.

A therapy device 100 according to a first embodiment will be described with reference to FIGS. 1A, 1B, 2, 3, and 4. While FIG. 3 is a cross-sectional view of the therapy device 100 and a living-body internal part 902, only the therapy device 100 is shown in thin black, but the living-body internal part 902 is not shown in thin black. In FIGS. 3 and 4, a filter 40 is exaggeratedly illustrated with a thickness larger than the actual one. In FIGS. 1A, 1B and 2, the height direction is taken as an upward direction and a direction opposite from the height direction is taken as a downward direction.

The therapy device 100 is used for a negative pressure wound therapy that accelerates recovery of a wound site by applying a negative pressure to a surface of the wound site.

As illustrated in FIG. 1A, the therapy device 100 includes a wound dressing 10 and a pump unit 20. The pump unit 20 is fixed to an upper surface (a surface in the height direction) of the wound dressing 10. As illustrated in FIG. 1B, a user 900 uses the therapy device 100 while the wound dressing 10 and the pump unit 20, which are combined by fixing, are stuck and worn on a skin surface 901 to cover a wound site. However, the therapy device 100 may be worn, for example, by being wound around the leg of the user with a band instead of being stuck.

The pump unit 20 is thin and is shorter in the height direction than in the width direction and the depth direction. The pump unit 20 is superposed on a center portion of the wound dressing 10 when the therapy device 100 is viewed in plan. While the pump unit 20 is smaller than the wound dressing 10 in plan view in FIG. 1A, it may be either smaller or larger than the wound dressing 10 as long as it is superposed on the center portion of the wound dressing 10. Structures of the pump unit 20 will be described later.

As illustrated in FIG. 2, the wound dressing 10 includes a drape 11, an absorbing member 13, a covering member 15, and a gauze piece 14. The gauze piece 14, the covering member 15, the absorbing member 13, and the drape 11 are arranged in order in the height direction.

The drape 11 is a film that prevents passage of liquid and gas. The absorbing member 13 absorbs liquid and holds the absorbed liquid. As the absorbing member 13, for example, cotton and a gel in which highly water-absorbing polymers are dispersed can be used. The covering member 15 is formed of a porous material that allows passage of liquid. As the covering member 15, for example, polyurethane foam that is easily formed according to the shape of the wound site can be used.

The pump unit 20 includes a housing 22. As illustrated in FIG. 2, a lower surface of the housing 22 is opposed to an upper surface of the drape 11. The housing 22 has, on the lower surface, a joint portion (an area shown in thin black in FIG. 2) joined to the upper surface of the drape 11. For example, the joint portion and the upper surface of the drape 11 are joined with an adhesive tape stuck on the lower surface of the housing 22 beforehand. By this joining, the housing 22 is fixed to the drape 11. However, this joining may be carried out with members other than the adhesive tape.

As illustrated in FIG. 2, the drape 11 has an opening 12 in its center. The housing 22 has an inlet 21 in its lower surface. The opening 12 and the inlet 21 are provided in an inner side portion of the joint portion between the housing 22 and the drape 11 when the therapy device 100 is viewed in plan. In other words, the joint portion between the housing 22 and the drape 11 is provided in an outer side portion of the opening 12 and the inlet 21 when the therapy device 100 is viewed in plan. While the inlet 21 is illustrated as one opening in FIG. 2, for example, it may be formed by a mesh composed of a plurality of apertures.

The therapy device 100 has the filter 40 that does not allow passage of liquid, but allows passage of gas. The opening 12 and the inlet 21 are opposed to each other with the filter 40 interposed therebetween. The filter 40 is larger than the opening 12 and the inlet 21 in plan view. However, the filter 40 may be disposed on the side of the wound dressing 10 and on the side of the housing 22 instead of being disposed between the wound dressing 10 and the housing 22 as long as liquid does not flow into the housing 22 through the inlet 21.

As illustrated in a sectional side view of FIG. 3, the therapy device 100 is worn by the user 900 to cover a wound site shown in an area 903 (hereinafter referred to as wound site 903) so that the height direction is opposite from the subcutaneous direction of the wound site 903.

Specifically, an outer peripheral portion of the drape 11 is stuck on the skin surface 901 in an outer side portion of the wound site 903 when the therapy device 100 is viewed in plan. For example, the drape 11 is stuck on the skin surface 901 with an adhesive material applied on a lower surface of the drape 11. Thus, the drape 11 and the wound site 903 form a closed space 904, as illustrated in FIG. 3.

The gauze piece 14 is disposed in contact with a surface of a wound bed 905 in an inner side portion of the wound site 903 when the therapy device 100 is viewed in plan. After the covering member 15 is formed according to the shape of the wound bed 905, it is placed on an upper side of the gauze piece 14 to fill the wound bed 905. The absorbing member 13 is disposed on an upper side of the covering member 15 to be opposed to the opening 12 when the therapy device 100 is viewed in plan.

Next, as illustrated in an enlarged view of FIG. 4, the pump unit 20 includes a battery 24 and a suction chamber 30. The battery 24 supplies power to an electric structure (for example, a piezoelectric pump 36) to be described later.

The suction chamber 30 is provided inside the housing 22. The inlet 21 of the housing 22 communicates with the suction chamber 30. That is, the suction chamber 30 communicates with the closed space 904 through the inlet 21 and the opening 12 in order. A substrate 28 is disposed on an outer surface of the suction chamber 30 in the height direction. A controller 32 is mounted on the substrate 28. A pressure sensor 34 is mounted on the substrate 28. The pressure sensor 34 has a nozzle inserted in the suction chamber 30. The pressure sensor 34 outputs a detection signal according to the value of pressure at a tip of the nozzle. However, the substrate 28, the controller 32, and the pressure sensor 34 may be disposed at other positions as long as the tip of the nozzle of the pressure sensor 34 is inserted in the suction chamber 30.

A piezoelectric pump 36 is disposed on an inner surface of the suction chamber 30 in the height direction. The piezoelectric pump 36 includes a suction port and a nozzle inserted in an outer side portion of the suction chamber 30 (an outer side portion in the height direction in FIG. 4). However, it is only necessary that the suction port should communicate with the suction chamber 30 and a tip of the nozzle should communicate with the outer side portion of the suction chamber 30, and the piezoelectric pump 36 may be disposed at other positions. To increase the suction flow rate, a plurality of piezoelectric pumps 36 may be provided.

The piezoelectric pump 36 includes a vibration plate having a first principal surface and a second principal surface and a piezoelectric element provided on at least one of the first principal surface and the second principal surface of the vibration plate (the vibration plate and the piezoelectric element are not illustrated). When an alternating voltage is applied to the piezoelectric element, the piezoelectric element repeats expansion and contraction in the principal surface direction of the vibration plate. The vibration plate makes bending vibrations along with expansion and contraction of the piezoelectric element. The piezoelectric pump 36 transports gas from the suction port of the suction chamber 30 to the tip of the nozzle in the outer side portion of the suction chamber 30 by utilizing the vibrations of the vibration plate. Thus, a negative pressure is generated in the suction chamber 30. The gas discharged from the nozzle of the piezoelectric pump 36 is discharged from, for example, a vent hole 26 provided in an upper surface of the housing 22.

The size and height of the piezoelectric pump 36 are less than, for example, those of an electromagnetic pump using the current and the magnetic field. Therefore, the housing 22 is reduced in size and height because the pump unit 20 includes the small and low-height piezoelectric pump 36.

Vibrations of the piezoelectric pump 36 are smaller than vibrations of the electromagnetic pump and the like. Further, when the alternating voltage applied to the piezoelectric element in the piezoelectric pump 36 has a frequency (for example, 20 kHz or more) higher than the audible frequency band, vibration noise of the vibration plate in the piezoelectric pump 36 is not easily heard by the user 900.

However, the pump unit 20 may include a piezoelectric pump that sucks gas from the tip of the nozzle, instead of the piezoelectric pump 36 that discharges gas from the tip of the nozzle. In this case, the piezoelectric pump that sucks gas from the tip of the nozzle is disposed so that the tip of the nozzle is inserted in the suction chamber 30 and a discharge port is located in an outer side portion of the suction chamber 30.

In the embodiment, it is not essential to provide the piezoelectric pump 36. The pump unit 20 may include, for example, an electromagnetic pump instead of the piezoelectric pump 36.

The controller 32 adjusts the pressure value of the suction chamber 30, for example, into a range of 75 to 125 mmHg by subjecting the piezoelectric pump 36 to feedback control using the pressure value of the suction chamber 30 represented by a detection signal output from the pressure sensor 34.

The controller 32 and the piezoelectric pump 36 are electrically connected through an electrode terminal insert-molded in the suction chamber 30. The nozzles of the pressure sensor 34 and the piezoelectric pump 36 are inserted with O-rings, and this enhances sealability.

Figure 5:
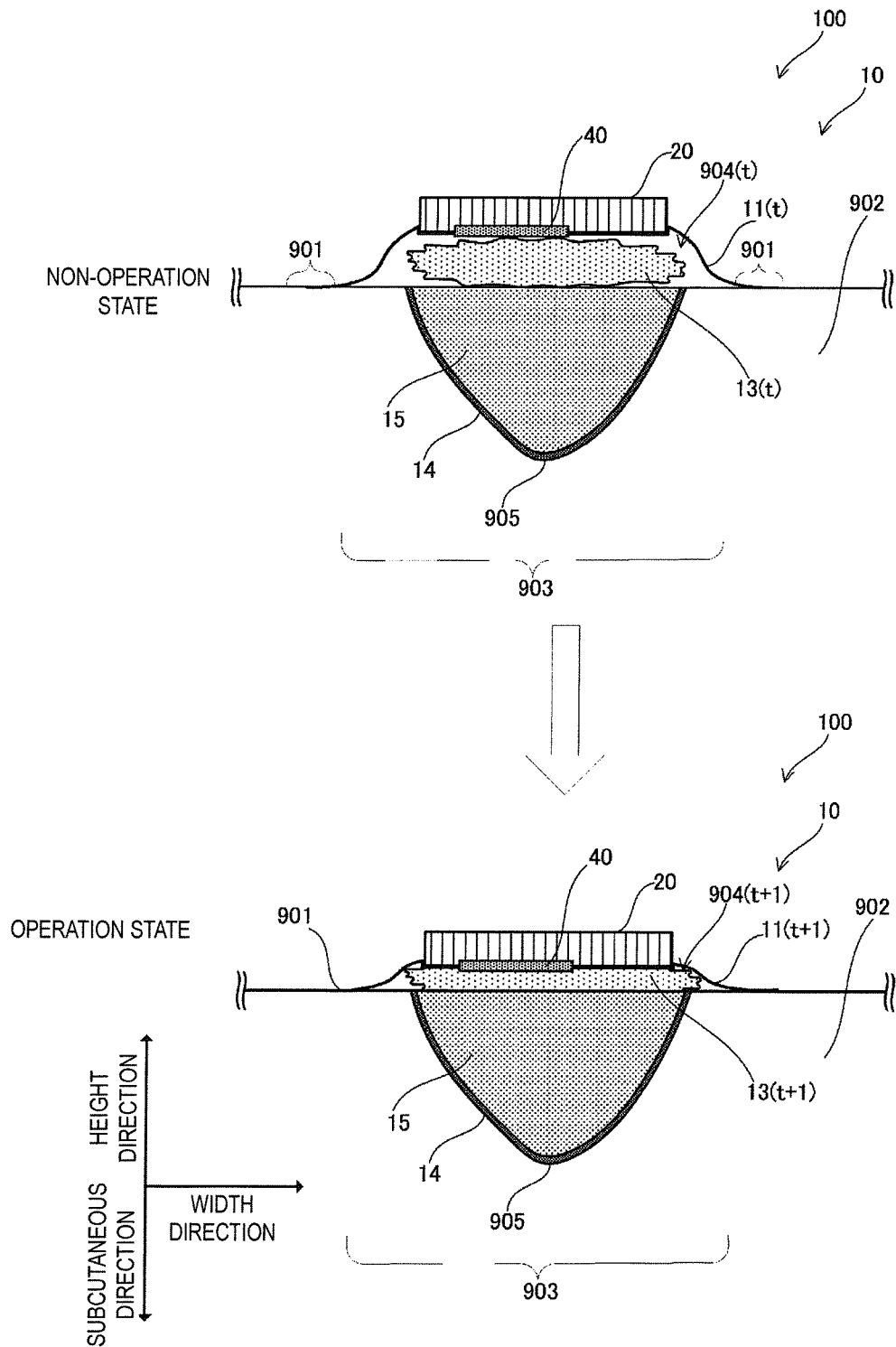
FIG. 5 includes sectional side views of the therapy device of the first embodiment in a non-operation state and an operation state, which illustrate the operation of the therapy device.

As illustrated in FIG. 5, in a state in which the therapy device 100 is only worn, but is not operated, the closed space 904($t$) formed by the drape 11($t$) and the wound site 903 contains gas. When the controller 32 drives the piezoelectric pump 36, the pressure in the suction chamber 30 gradually becomes a negative pressure. The pressure in the closed space 904($t$) communicating with the suction chamber 30 also gradually becomes a negative pressure. Then, the gas contained in the closed space 904($t$) is discharged from the closed space 904($t$) to the outside of the therapy device 100 while passing through the suction chamber 30, the piezoelectric pump 36, and the vent hole 26 in order. Thus, the drape 11(*t*+1) gradually deforms, and the closed space 904(*t*+1) gradually becomes small.

When the controller 32 further continues to drive the piezoelectric pump 36, an exudate from the wound bed 905, which is contained in the gauze piece 14 and the covering member 15, flows to the absorbing member 13 on the negative pressure side (the side of the opening 12), and is absorbed by the absorbing member 13.

As described above, in this embodiment, the housing 22 of the pump unit 20 is fixed to the drape 11 of the wound dressing 10 by the joint portion. Since the suction chamber 30 to be brought into a negative pressure by driving of the piezoelectric pump 36 directly communicates with the closed space 904 through the opening 12 and the inlet 21, the therapy device 100 does not need to include a pipe that allows the pump unit 20 to communicate with the closed space 904. Therefore, since the therapy device 100 of the embodiment does not need to include the pipe that allows the pump unit 20 to communicate with the closed space 904, detachment of the pump unit 20 from the wound dressing 10 due to coming-off of the pipe is is avoided. Since the housing 22 is fixed to the drape 11 by the joint portion, the pump unit 20 can be prevented from detaching from the wound dressing 10.

The absorbing member 13 may be provided on the side of the pump unit 20 instead of the side of the wound dressing 10. Specifically, in the pump unit 20, the suction port of the piezoelectric pump 36 may be covered with the filter 40 and the absorbing member 13 may be provided, for example, inside the suction chamber 30.

However, when the wound dressing 10 has the absorbing member 13 in the closed space 904, the pump unit 20 does not need to include the absorbing member 13. Hence, the size of the pump unit 20 is not increased by provision of the absorbing member 13.

The piezoelectric pump 36 preferably includes a check valve that prevents gas from flowing from the tip of the nozzle in the outer side portion of the suction chamber 30 to the suction port inside the suction chamber 30. Thus, in the therapy device 100, for example, even when power supply from the battery 24 is stopped and the piezoelectric pump 36 cannot be driven, the exudate from the absorbing member 13 can be prevented from flowing back to the wound bed 905 owing to backflow of the gas to the closed space 904.

While the pump unit 20 is opposed to the wound site 903 with the wound dressing 10 interposed therebetween in the height direction in the example of FIG. 3, it may be disposed as follows.

As illustrated in a sectional side view of FIG. 6, in a therapy device 100A according to a modification of the therapy device 100, a pump unit 20 is disposed apart from a wound site 903 in the surface direction of a skin surface 901. More specifically, an opening 12A of a drape 11A is provided apart from the wound site 903 in the width direction. An absorbing member 13A is disposed from an upper side of a covering member 15 to the opening 12A.

In the therapy device 100A, the pump unit 20 is disposed apart from the wound site 903 in the surface direction of the skin surface 901. Hence, even when the pump unit 20 collides with an object around a user 900, it can be prevented from directly pressing the wound site 903. Further, when the drape 11A passes vapor from a closed space 904 to the atmosphere within a range such as to maintain the negative pressure in the closed space 904, the vapor in the closed space 904 easily passes through the drape 11A because the drape 11A just on the wound site 903 is not covered with the pump unit 20.

Figure 7A:
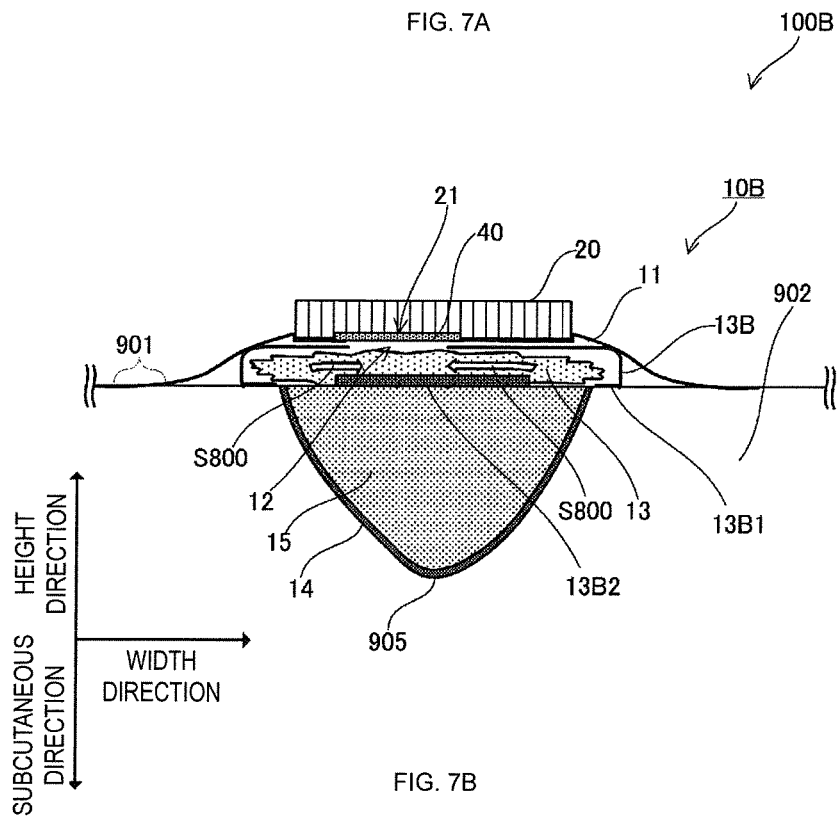
FIG. 7A is a sectional side view of a therapy device according to a second embodiment.

As illustrated in FIG. 7A, a therapy device 100B according to a second embodiment is different from the therapy device 100 of the first embodiment in that a wound dressing 10B includes a container 13B having an absorbing member 13 therein.

Descriptions of structures overlapping with those of the therapy device 100 are skipped.

Figure 7B:
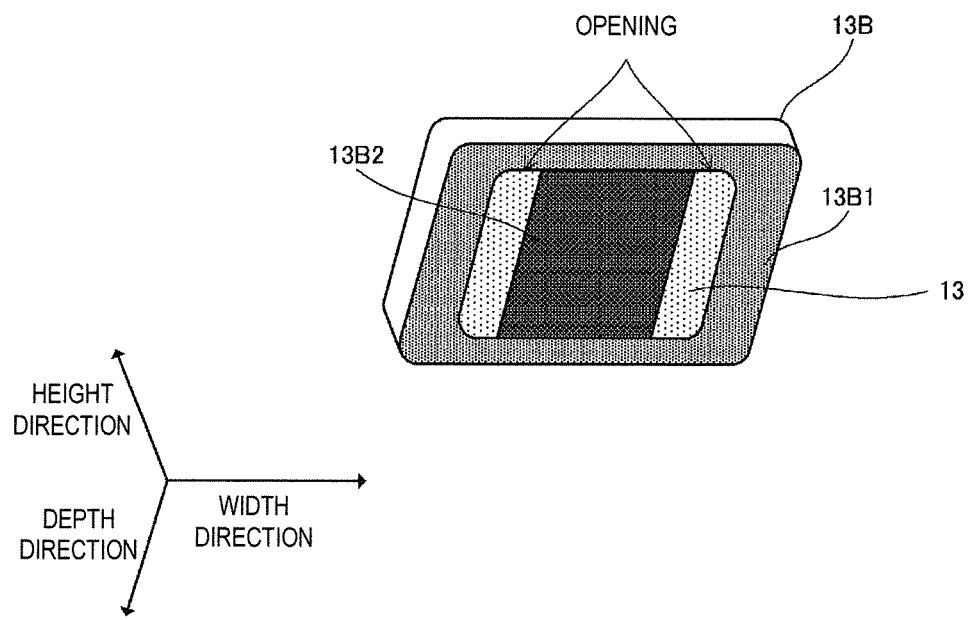
FIG. 7B is a perspective view of a container as viewed from the lower side.

As illustrated in FIGS. 7A and 7B, for example, the container 13B is shaped like a rectangular parallelepiped having a hollow portion, and has openings in upper and lower surfaces. The opening in the upper surface of the container 13B is opposed to an opening 12 of a drape 11.

As illustrated in FIG. 7B, the container 13B has an edge portion 13B1 and a silicon film 13B2 on the lower surface. As illustrated in FIG. 7A, the silicon film 13B2 is opposed to the opening 12 with the absorbing member 13 interposed therebetween. The silicon film 13B2 prevents passage of an exudate. Only two openings are provided in the container 13B with the silicon film 13B2 interposed therebetween in the width direction.

The container 13B is disposed so that the edge portion 13B1 is in contact with a portion of a skin surface in a wound site 903 other than a wound bed 905. Such arrangement of the container 13B prevents the wound bed 905 from being directly pressed in the subcutaneous direction.

The exudate from the wound bed 905 flows through a gauze piece 14 and a covering member 15 in order, but does not pass through the silicon film 13B2. Hence, the exudate flows from the two openings in outer side portions of the silicon film 13B2 in the width direction toward the opening 12 of the drape 11 inside the absorbing member 13. That is, the wound dressing 10B forms flow passages (shown by open arrows 5800 in FIG. 7A) in which the exudate flows from the outer side portion toward the inner side portion of the absorbing member 13 in the width direction. Since the flow passages are formed by the silicon film 13B2 in the wound dressing 10B, the exudate can be prevented from flowing only to a part of the absorbing member 13 (for example, a widthwise center portion opposed to the opening 12). This can increase the volume of the absorbing member 13 through which the exudate passes.

Since the container 13B contains the absorbing member 13 in the wound dressing 10B, the exudate can be easily disposed of.

For example, the container 13B is formed of resin such as PET. However, the material of the container 13B is not limited to the resin, but may be metal. The material of the container 13B may have or not have a hardness such as not to be deformed by the weight of the exudate absorbed by the absorbing member 13. Further, the container 13B does not always need to have the edge portion 13B1.

In the wound dressing 10B, only the silicon film 13B2 may be provided between the covering member 15 and the absorbing member 13 without using the container 13B. Even when only the silicon film 13B2 is provided, since the wound dressing 10B forms the flow passages for the exudate, the volume of the absorbing member 13 through which the exudate passes can be increased.

However, the flow passages shown by open arrows 5800 in FIG. 7A are just exemplary, and can be appropriately changed, for example, according to the shape of the absorbing member 13 and the position of the opening 12 by changing the shape of the silicon film 13B2.

As illustrated in FIG. 8, a therapy device 100C according to a third embodiment is different from the therapy device 100 of the first embodiment in that a suction pad 23 is provided and in that a suction chamber 30 has a suction port 33. Descriptions of structures overlapping with those of the therapy device 100 are skipped. FIG. 8 illustrates a state before the suction pad 23 is suctioned onto a drape 11.

A lower surface of the suction pad 23 is suctioned onto an upper surface of the drape 11. More specifically, the suction pad 23 includes a body portion 23C1 and a bowl-shaped portion 23C2 that are joined together. For example, the body portion 23C1 is joined to an upper surface of a housing 22 of a pump unit 20. The bowl-shaped portion 23C2 is provided on an outer periphery of the housing 22 in plan view, and is curved to be convex to the outside of the housing 22 in the height direction. The bowl-shaped portion 23C2 is formed of an elastically deformable material (for example, elastic rubber). The bowl-shaped portion 23C2 is deformed by being pressed against the drape 11, and gas is released outside from a closed space formed by the bowl-shaped portion 23C2, the drape 11, and the housing 22, so that the suction pad 23 generates a negative pressure in the closed space.

For example, the suction port 33 is provided on a lower side of a joint portion between the body portion 23C1 and the bowl-shaped portion 23C2 in a side surface of the housing 22. However, it is only necessary that the suction port 33 should communicate with the closed space formed by the bowl-shaped portion 23C2, the drape 11, and the housing 22, and may be provided in a lower surface of the housing 22 within a range such as to maintain sealing of an opening 12 of the drape 11.

In the therapy device 100C, gas is sucked by a piezoelectric pump 36 not only from an inlet 21 but also from the suction port 33. Thus, a negative pressure is generated in the closed space formed by the bowl-shaped portion 23C2, the drape 11, and the side surface of the housing 22. Therefore, in the therapy device 100C, the closed space is further brought into a negative pressure by suction of the suction pad 23 and suction of the piezoelectric pump 36. Hence, the housing 22 of the pump unit 20C is more reliably fixed to the drape 11. Thus, the pump unit 20C is less likely to detach from a wound dressing 10.

In the therapy device 100C, however, the housing 22 may be fixed to the drape 11 only with the suction pad 23 without forming the suction port 33 in a suction chamber 30A. Further, in the therapy device 100C, the pump unit 20C may be fixed to the drape 11 only with the suction pad 23 without using an adhesive tape that sticks the lower surface of the housing 22 and the upper surface of the drape 11.

Figure 9:
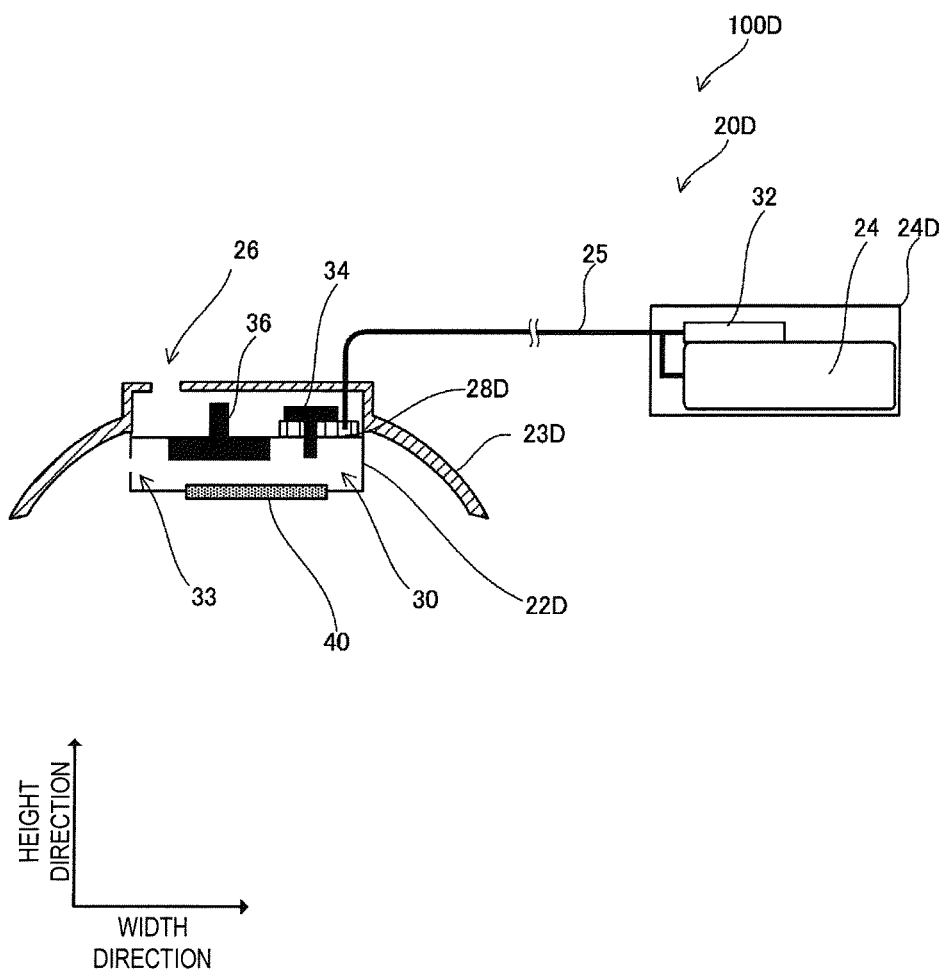
FIG. 9 is an enlarged sectional side view of a therapy device according to a fourth embodiment.

As illustrated in FIG. 9, in a therapy device 100D according to a fourth embodiment, the size of a housing 22D is reduced because the electric structures in the therapy device 100C of the third embodiment are stored in a second housing 24D.

More specifically, the second housing 24D stores a battery 24 and a controller 32. The battery 24 and the controller 32 in the second housing 24D are electrically connected to a substrate 28D in the housing 22D through an electric wire 25.

In the therapy device 100D, the sizes of the housing 22D and the substrate 28D are reduced because the second housing 24D contains the battery 24 and the controller 32. The size of a suction pad 23D is also reduced by size reduction of the housing 22D.

In the therapy device 100D, even when a pump unit 20D includes two housings (housing 22D and second housing 24D), since there is no need to include a pipe that allows the pump unit 20D to communicate with a closed space 904, the pump unit 20D is not detached from a wound dressing 10 owing to coming-off of the pipe.

Further, in the therapy device 100D, since the second housing 24D is electrically connected to the housing 22D through the electric wire 25, it can be disposed apart from the housing 22D. That is, the therapy device 100D allows the second housing 24D to be disposed apart from a wound site 903. Therefore, in the therapy device 100D, since the battery 24 and the controller 32 provided in the second housing 24D can be replaced and repaired at the position apart from the wound site 903, replacement and repair of the battery 24 and the controller 32 can be simplified.

10, 10B wound dressing
11, 11A drape
12, 12A opening
13, 13A absorbing member
13B container
13B1 edge portion
13B2 silicon film
14 gauze piece
15 covering member
20, 20C, 20D pump unit
21 inlet
22, 22D housing
23, 23D suction pad
23C1 body portion
23C2 bowl-shaped portion
24 battery
24D second housing
25 electric wire
26 vent hole
28, 28D substrate
30 suction chamber
32 controller
33 suction port
34 pressure sensor
36 piezoelectric pump
40 filter
100, 100A, 100B, 100C, 100D therapy device

The invention claimed is:

1. A negative pressure wound therapy device comprising:
a wound dressing including a drape having an opening and adapted for close contact with an outer periphery of a wound site on an outer periphery of the opening; and
a pump unit including a housing and a pump, wherein the housing includes:
a joint portion joined to the drape, and
an inlet communicating with a suction port of the pump in an inner side portion of the joint portion,
wherein the suction port of the pump is adapted for communicating with a closed space formed by the drape and the wound site via the opening of the drape and the inlet of the housing,
wherein the negative pressure wound therapy device further includes an absorbing member adapted for being disposed in the closed space to absorb a liquid, and an exudate passage preventing member at a position opposed to the opening with the absorbing member interposed between the exudate passage preventing member and the opening, and
wherein the absorbing member is configured to absorb and store exudate from the wound site.

2. The negative pressure wound therapy device according to claim 1, wherein the exudate passage preventing member and the inlet are overlapped each other.

3. The negative pressure wound therapy device according to claim 1, wherein the pump unit includes a suction pad fixing the housing to the drape by suction.

4. The negative pressure wound therapy device according to claim 1,
wherein the housing includes a pressure sensor detecting a pressure value in the suction chamber, and
wherein the pump unit includes:
a battery supplying a power to the pump and the pressure sensor,
a controller controlling a driving of the pump according to the pressure value detected by the pressure sensor, and
a second housing storing the battery and the controller and electrically connected to the housing through a wire.

5. The negative pressure wound therapy device according to claim 4, wherein the pump includes a check valve preventing a backflow of a fluid.

6. The negative pressure wound therapy device according to claim 1, wherein the pump is driven by a piezoelectric element.

7. The negative pressure wound therapy device according to claim 3,
wherein the housing includes a pressure sensor detecting a pressure value in the suction chamber, and
wherein the pump unit includes:
a battery supplying a power to the pump and the pressure sensor,
a controller controlling a driving of the pump according to the pressure value detected by the pressure sensor, and
a second housing storing the battery and the controller and electrically connected to the housing through a wire.

8. The negative pressure wound therapy device according to claim 3, wherein the pump is driven by a piezoelectric element.

9. The negative pressure wound therapy device according to claim 4, wherein the pump is driven by a piezoelectric element.

10. The negative pressure wound therapy device according to claim 5, wherein the pump is driven by a piezoelectric element.

11. The negative pressure wound therapy device according to claim 1, wherein the suction chamber is adapted for directly communicating with a closed space formed by the drape and the wound site via the opening of the drape and the inlet of the housing.

12. The negative pressure wound therapy device according to claim 1, further comprising two flow openings configured to allow exudate to flow from the wound site to the absorbing member.

13. The negative pressure wound therapy device according to claim 12, wherein the two flow openings are provided on opposite sides of the exudate passage preventing member.

14. The negative pressure wound therapy device according to claim 12, further comprising a container disposed in the closed space that contains the absorbing member and defines the two flow openings.

15. The negative pressure wound therapy device according to claim 1, further comprising a filter, wherein the absorbing member is interposed between the filter and the exudate passage preventing member.

16. The negative pressure wound therapy device according to claim 2, wherein the exudate passage preventing member and the inlet are overlapped each other in a plan view of the wound site.

17. The negative pressure wound therapy device according to claim 2, wherein the exudate passage preventing member and the inlet are overlapped each other in a stacking direction of the wound dressing and pump unit.

\* \* \* \* \*

UNITED STATES PATENT AND TRADEMARK OFFICE
CERTIFICATE OF CORRECTION

PATENT NO. : 11,806,469 B2
APPLICATION NO. : 16/919172
DATED : November 7, 2023
INVENTOR(S) : Masaaki Fujisaki It is certified that error appears in the above-identified patent and that said Letters Patent is hereby corrected as shown below:

In the Specification

Column 8, Line 33, "5800" should be -- S800 --.

Column 8, Line 59, "5800" should be -- S800 --.

Signed and Sealed this
Thirteenth Day of August, 2024

Katherine Kelly Vidal
*Director of the United States Patent and Trademark Office*